United States Patent [19]

Marin et al.

[11] Patent Number: 5,569,296
[45] Date of Patent: Oct. 29, 1996

[54] METHOD FOR DELIVERING AND DEPLOYING INTRALUMINAL DEVICES

[75] Inventors: Michael L. Marin; Ralph Marin, both of New York, N.Y.

[73] Assignee: Stentco, Inc., Cross River, N.Y.

[21] Appl. No.: 483,191

[22] Filed: Jun. 7, 1995

Related U.S. Application Data

[63] Continuation-in-part of Ser. No. 243,190, May 13, 1994, Pat. No. 5,456,694.

[51] Int. Cl.⁶ ................................................. A61M 29/00
[52] U.S. Cl. .......................... 606/198; 604/96; 606/194; 623/1; 623/12
[58] Field of Search .............................. 606/108, 1, 191, 606/192, 194, 195, 198, 200; 128/898, 899; 623/1, 11, 12; 604/96

[56] References Cited

U.S. PATENT DOCUMENTS

| | | |
|---|---|---|
| 3,657,744 | 4/1972 | Ersek . |
| 4,787,899 | 11/1988 | Lazarus . |
| 5,190,058 | 3/1993 | Jones et al. . |
| 5,316,023 | 5/1994 | Palmaz et al. ........................... 623/1 |
| 5,370,657 | 12/1994 | Irie ....................................... 606/200 |

FOREIGN PATENT DOCUMENTS

| | | | |
|---|---|---|---|
| 0461791 | 12/1991 | European Pat. Off. ................... 623/1 |
| 0551179 | 7/1993 | European Pat. Off. . |
| 0596145 | 5/1994 | European Pat. Off. . |

Primary Examiner—Michael Powell Buiz
Assistant Examiner—William Lewis
Attorney, Agent, or Firm—Darby & Darby, P.C.

[57] ABSTRACT

A method for delivering and deploying an intraluminal device. A guidewire is inserted such that one end extends into the patient at an entrance point and the other end extends out of the patient through an exit point. First and second catheters are then passed over the guidewire. The first and second catheters are connected to each other so that the transluminal device may be positioned within the blood vessel by pushing one catheter and pulling the other catheter.

4 Claims, 8 Drawing Sheets

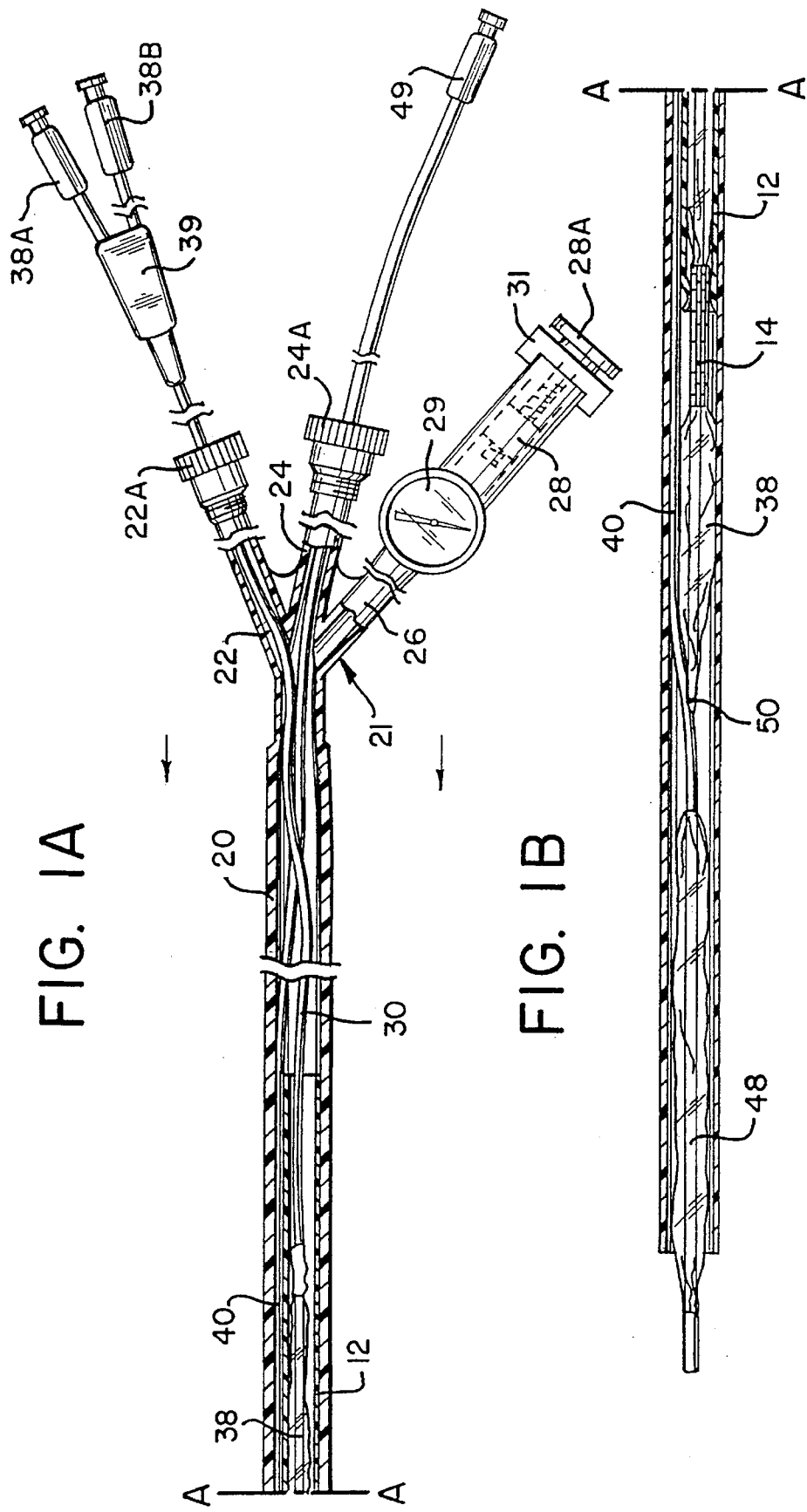

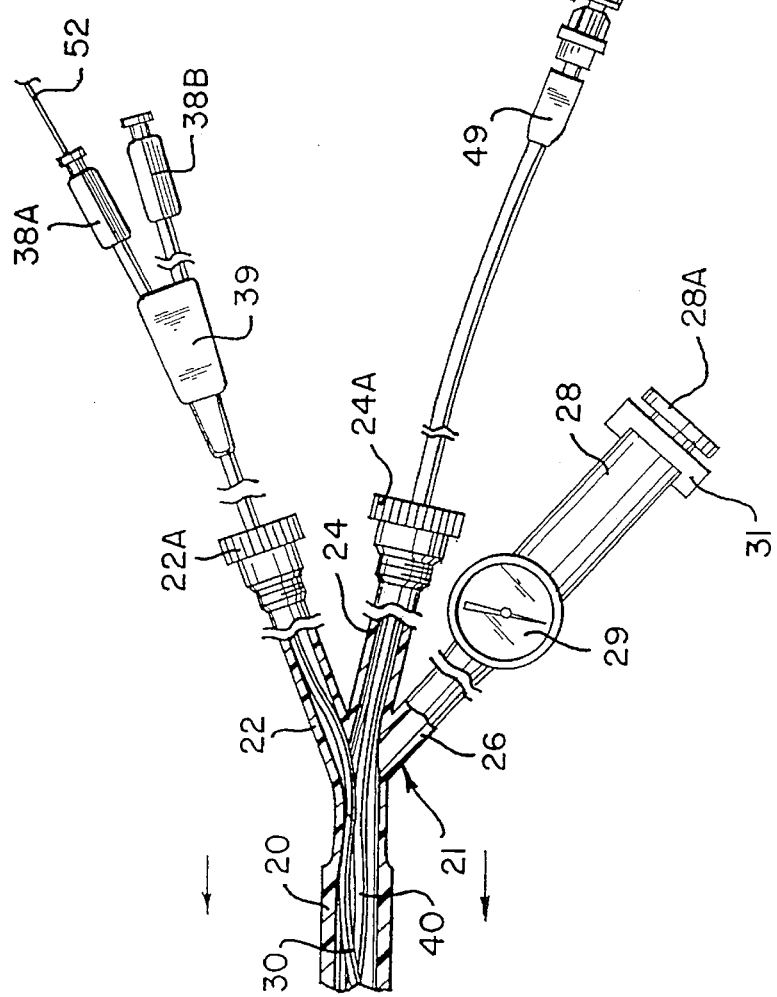
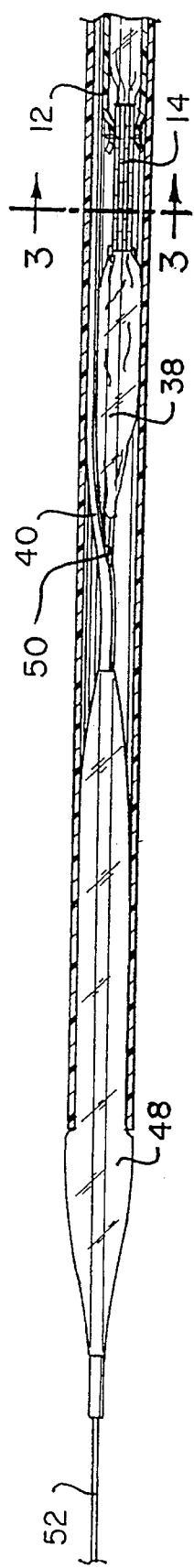
FIG. 2A
FIG. 2B

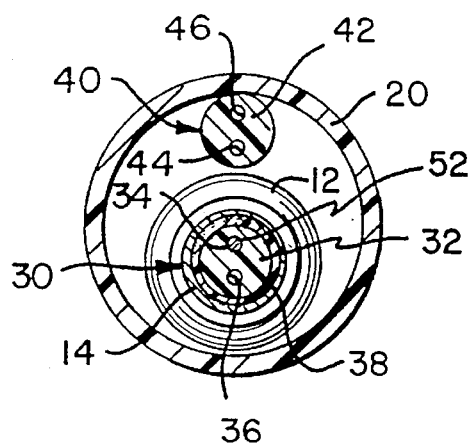
FIG. 3
FIG. 4
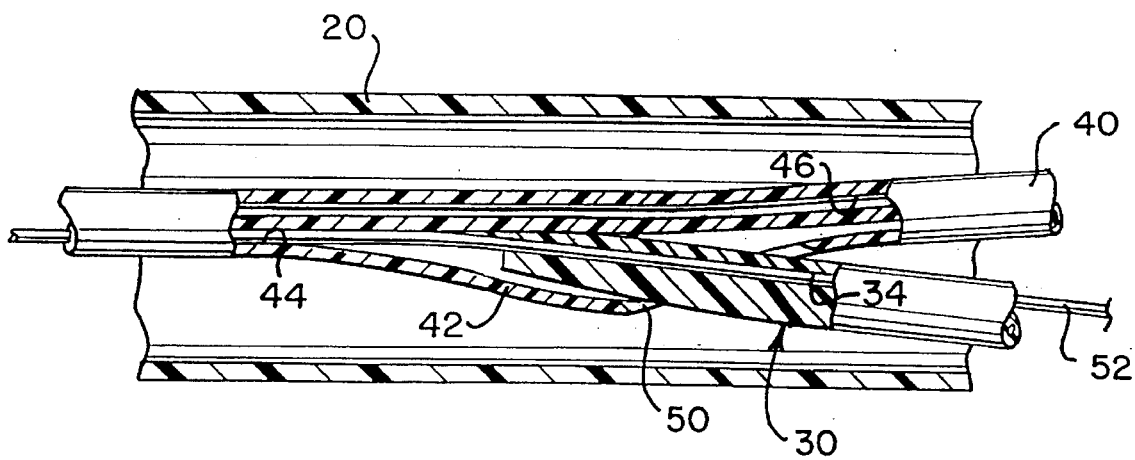

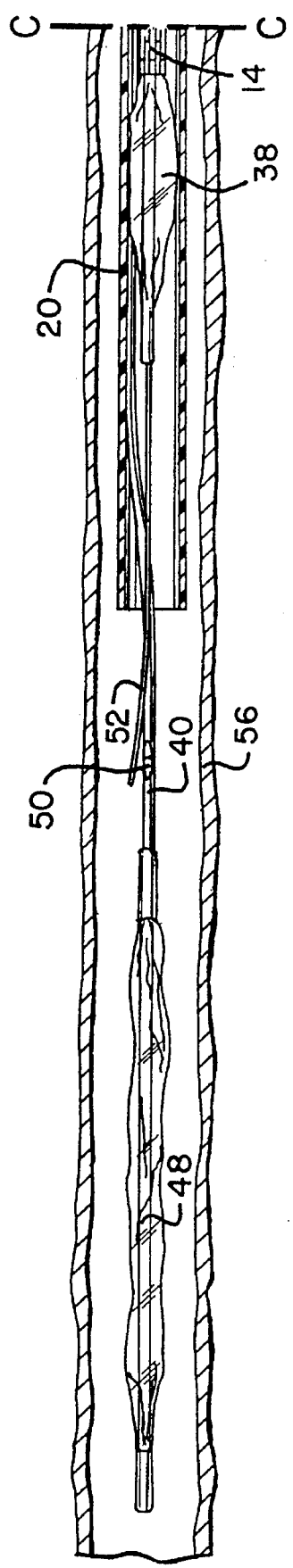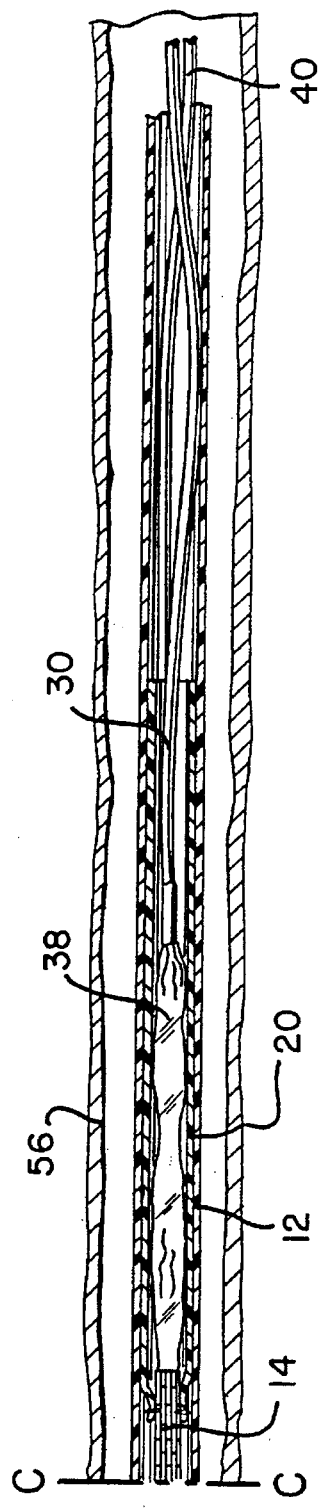

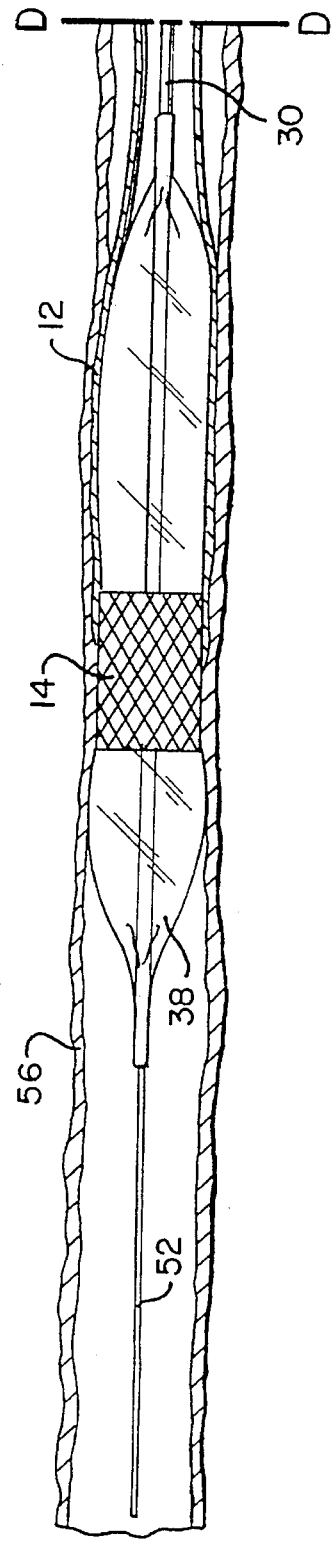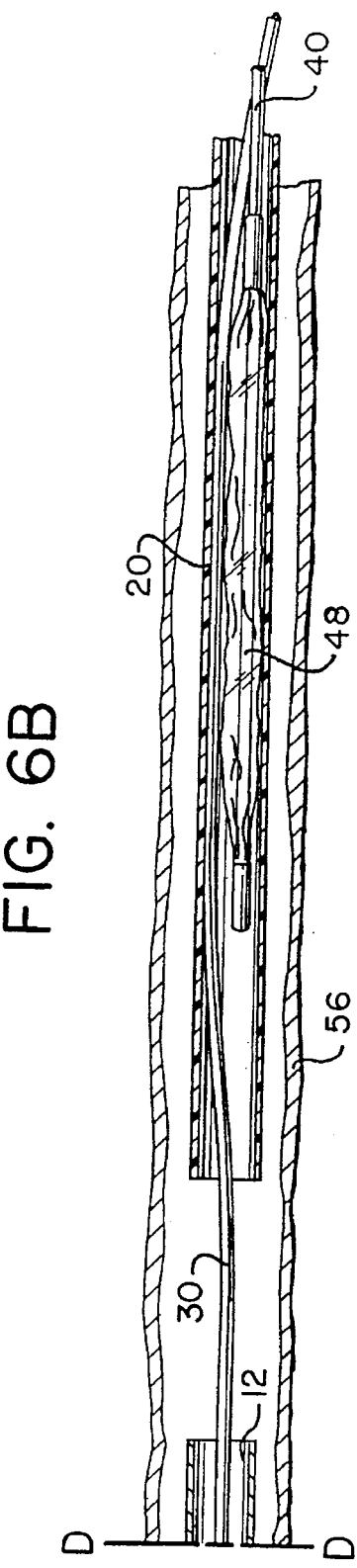

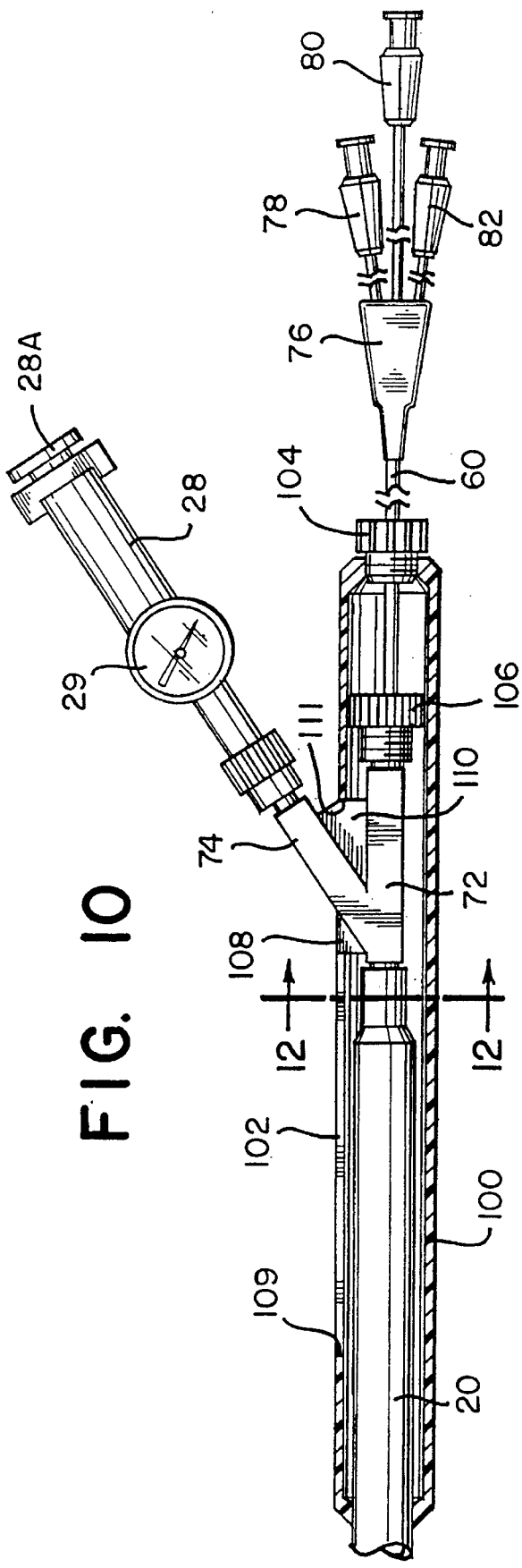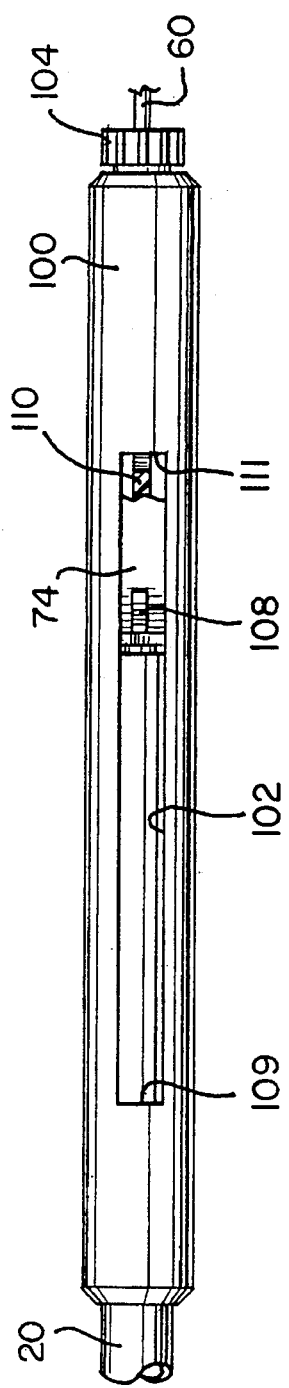
FIG. 10
FIG. 11

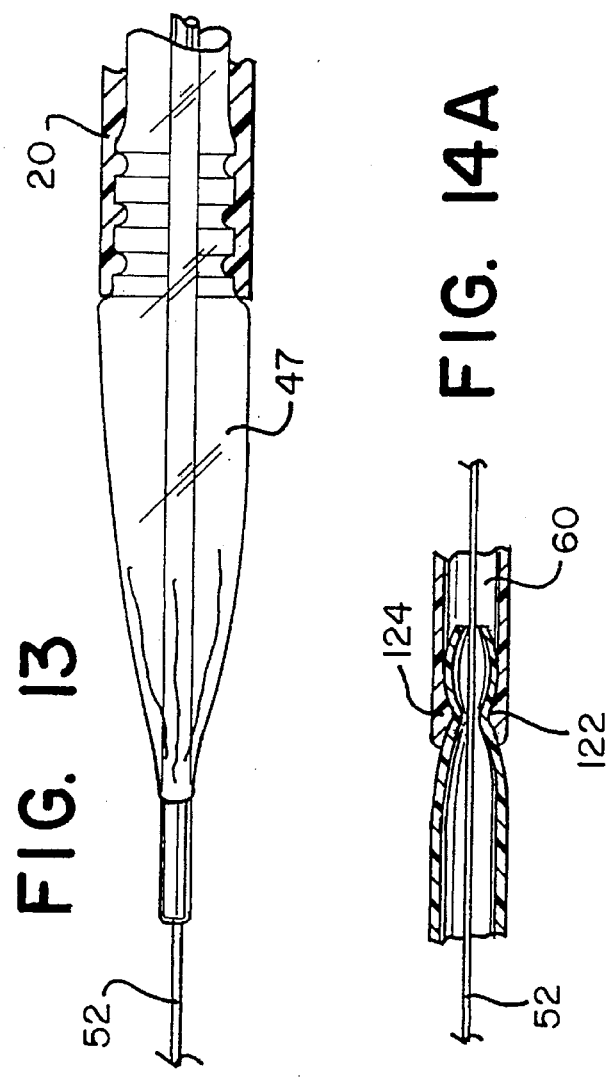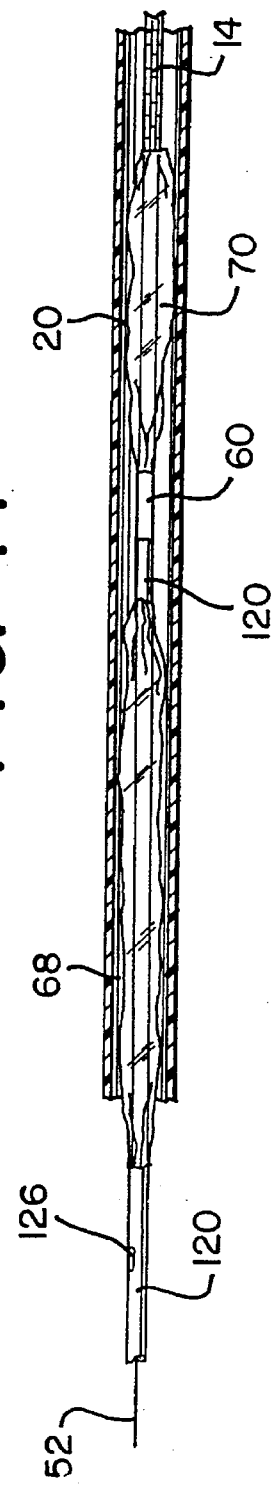

METHOD FOR DELIVERING AND DEPLOYING INTRALUMINAL DEVICES

This is a continuation-in-part of U.S. patent application Ser. No. 08/243,190, filed May 13, 1994, entitled Method for Delivering and Deploying Intraluminal Devices, now U.S. Pat. No. 5,456,964.

This invention relates to a method of delivering and deploying an intraluminal device. The invention has particular utility in delivering and deploying stents and endovascular grafts within a blood vessel.

An endovascular graft is placed within a blood vessel and serves as a conduit for blood flow to exclude a vascular occlusion, aneurysm or other vessel abnormity. It may be made of a variety of materials, but most commonly is made of dacron, expanded polytetrafluoroethylene (ePTFE) or human vein. It is necessary to anchor the graft within the lumen of the blood vessel and this can be accomplished by means of an intravascular stent which is also commonly used to hold open diseased or occluded arteries. There are a number of known stents; some are of the self-expanding type and some are made of a material (for example metal) which can be expanded after the stent is in place to frictionally engage the blood vessel. Palmaz U.S. Pat. No. 4,776,337 illustrates in FIGS. 2A and 2B a stent of the latter type which is currently in use. As used herein, the term "graft stent complex" is intended to include the combination of a graft and one or more stents.

The delivery and deployment systems for a graft stent complex typically includes a guide sheath (catheter) which is properly positioned within the vasculature to guide the passage of a deployment mechanism (commonly a balloon catheter supporting the graft stent complex) to the proper site. The guide sheath have a relatively large diameter resulting in difficulty passing the sheath through arteries which usually are not straight and may have many curves or twists in them. Also, arteries may contain areas of disease (atherosclerotic plaque) which may obstruct the passage of the guide sheath through the vascular tree. Irregularly shaped plaque which could accidentally engage an endoluminal catheter may create potential sites for arterial injury. Further, the vasculature may contain segments which are weaker than others, putting them at risk for perforation should they engage the guide sheath as it is being moved along the arterial wall.

The conventional technique for positioning a guide sheath within a blood vessel requires the use of a stylet (or mandrel or stiffening catheter as it is sometimes called), which includes a tapered distal end extending from the distal end of the guide sheath to enhance pushability of the guide sheath while providing a tapered distal face to ease passage of the guide sheath through the artery. The stylet, however, does not completely cover the relatively sharp edges of the guide sheath. Patients, therefore, are subject to arterial injury, and dislodgement of intraluminal thrombus and accumulated plaque on the arterial wall. This can lead to severe injury. Moreover, them is a trade-off between stiffness and flexibility. If the sheath is too stiff, movement through the artery is difficult. If it is too flexible, the sheath is difficult to push. Since the flexibility of the stylet is not adjustable, passage of the catheter through sharp turns in the vasculature can be very difficult, if not impossible. For example, the iliac artery is commonly kinked in patients with aortic aneurysm disease because of the frequent elongation of the vasculature during formation of the aneurysm. Manipulation of a wide guide sheath through such an artery using conventional techniques can be exceedingly difficult.

Also, conventional guide sheaths need to be large enough to permit ease of movement of an endovascular graft out of the sheath and into the vasculature. The sheath size has to be large enough to maintain a low coefficient of friction between the inner surface of the deployment catheter and the graft stent complex. Such large sheaths require large holes into the inserting blood vessel.

Finally, in the systems currently used for delivering a graft stent complex through a guide sheath, the balloon catheter containing the graft stent complex must be introduced through a hemostatic valve at the proximal end of the guide sheath and pushed through the entire length of the guide sheath (for example about sixty cm) to the deployment position. This can prove to be time consuming and difficult. In addition, the stent can be dislodged from the balloon while being pushed through the long guide sheath. This can result in the sharp metal stent perforating the deployment balloon. In either case, it is necessary to withdraw the balloon catheter and repeat the procedure.

FIGS. 1–9 show two devices for delivering and deploying Intraluminal devices such as stents which overcome the above problems. Those devices comprise a guide sheath and a lead balloon which, when inflated, seals the guide sheath and provides a tapered leading edge for the guide sheath. In the case of patients with a tortuous vasculature, i.e. an arterial system in which the blood vessels have many twists and turns, as is often the case with elderly patients, it can be extremely difficult to push the guide sheath through the vasculature.

Thus, there exists a need for an improved process which simplifies the delivery of an intraluminal device such as a stent or graft stent complex to a position within a patient's vasculature, which process is effective even though the vasculature is tortuous.

SUMMARY OF THE INVENTION

In accordance with the invention, a transluminal device is delivered into a blood vessel by first directing a guide wire through the vasculature with the guide wire extending from an entrance point and an exit point. A first catheter is then passed over the guide wire through the vasculature from one point to the other with the ends of the catheter protruding from the entrance and exit points. A second catheter containing the transluminal device is then connected to an end of the first catheter. The transluminal device is positioned within the vasculature by pushing on the second catheter and, simultaneously pulling the first catheter. By simultaneously pushing and pulling on the catheter containing the transluminal device, it is much easier to traverse a tortuous path which otherwise might be unpassable.

In the preferred embodiment, the second catheter is positioned within a guide sheath and the first catheter contains a lead balloon which provides a tapered leading surface for the guide sheath and seals the distal end of the guide sheath so that it can be selectively pressurized to optimize its properties of steerability and pushability.

IN THE DRAWINGS

FIGS. 1A and 1B comprise a plan view, partially in section, of a first embodiment of the invention assembled and ready for use prior to lead balloon inflation and sheath pressurization.

FIGS. 2A and 2B are slightly enlarged views of the proximal and distal ends, respectively, of the device shown in FIGS. 1A and 1B with a guide wire in place and the lead balloon at the distal end of the guide sheath inflated;

FIG. 3 is a cross sectional view along the line 3—3 of FIG. 2B;

FIG. 4 is an enlarged side sectional view showing the manner in which the distal end of the deployment catheter is joined to the lead balloon catheter;

FIGS. 5A and 5B are slightly enlarged views showing the device with the deployment balloon positioned within the guide sheath and the lead balloon deflated and extended off and beyond the guide wire;

FIGS. 6A and 6B are slightly enlarged views showing the balloons after the deployment balloon has been inflated to expand the distal stent with the deflated lead balloon previously retracted into the sheath.

Figure 9:
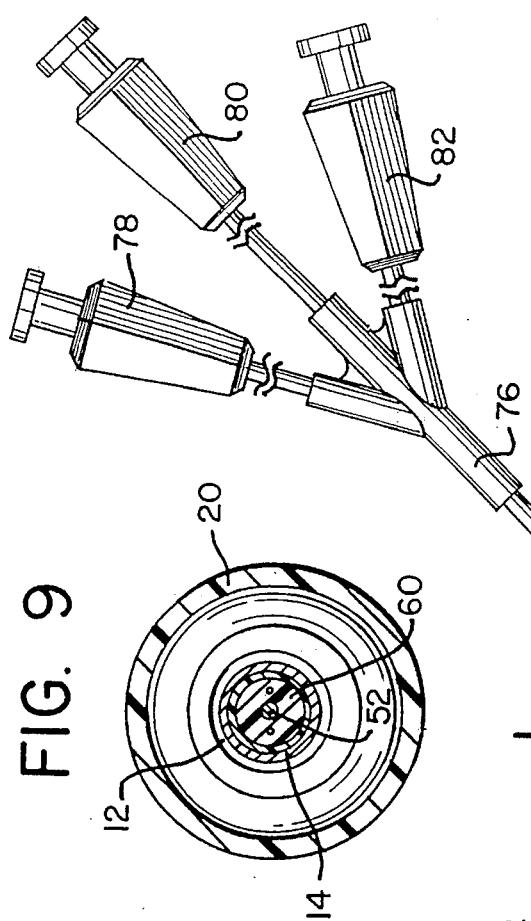
Figure 8:
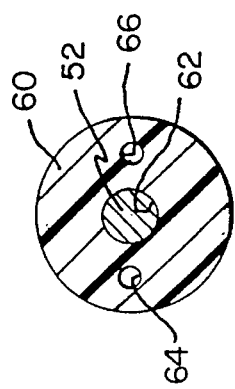
Figure 7A:
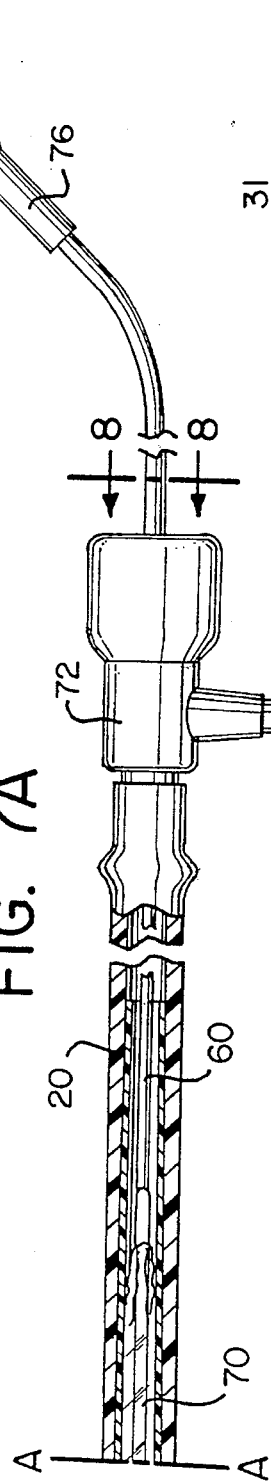
Figure 7B:
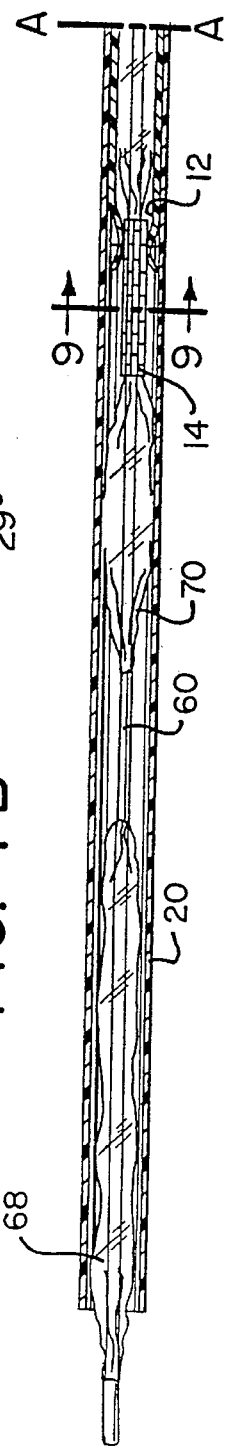

FIGS. 7A and 7B comprise a plan view partially in section showing a second embodiment of the invention;

FIG. 8 is a sectional view along the line 8—8 of FIG. 7A;

FIG. 9 is a sectional view along the line 9—9 of FIG. 7B;

FIG. 10 is a plan view partially in section of a handle according to the invention;

FIG. 11 is a top view of the handle;

FIG. 12 is a cross sectional view along the line 12—12 of FIG. 10;

FIG. 13 is an enlarged view of a lead balloon and sheath;

FIG. 14 is a plan view of a third embodiment in which the lead balloon is introduced into the distal end of the sheath and;

FIG. 14A is an enlarged side sectional view of the embodiment of FIG. 14 showing the manner in which the distal end of the deployment catheter is selectively joined to a lead balloon catheter.

DETAILED DESCRIPTION OF THE INVENTION

FIGS. 1–6 illustrate an embodiment of the invention in which separate deployment and lead balloon catheters are used to deploy a graft stent complex shown as comprising a graft 12 and stent 14. Stent 14, for example, may be a conventional Palmaz stent. The specific construction of the device to be deployed is not a feature of the invention.

The delivery and deployment device comprises a guide sheath 20 which is adapted to be positioned within the patient's vasculature to facilitate delivery of the graft stent complex to the location where it is to be deployed. The guide sheath 20 terminates at its proximal end in a three way hemostatic valve 21. Hemostatic valve 21 may be a modified Tuoy Borst hemostatic valve having deployment catheter port 22, an end catheter port 24 and a sheath pressurization port 26 for purposes described below. Hemostatic valve 21 prevents the loss of blood through sheath 20 when its distal end is not sealed. Thumb screws 22A and 24A close ports 22 and 24, also locking in position the catheter which passes through the port.

The sheath pressurization port 26 is connected through a syringe 28 which may be of the type which includes an integral infusion pressure manometer 29 to provide the operator with a continuous indication of the pressure applied by the syringe to the port 26. The syringe 28 may include a piston which is threadedly received within a bracket 31 fixed to the barrel. Pressure is applied by rotating a knob 28A at the end of the piston to advance the piston and apply very precise pressures to the sheath. Syringes of this type are conventional disposable items. The syringe may be integrally formed with the port 28, or the port and syringe may be provided with standard connecting means so that the parts can be selectively coupled together.

The guide sheath 20 contains a deployment catheter 30 and a lead balloon catheter 40. The deployment catheter 30 comprises an elongated flexible shaft 32 which includes a guide wire lumen 34 and an inflation lumen 36 (see FIG. 3). A deployment balloon 38 is mounted on the distal end of the deployment catheter 30 in such a way that it can be inflated and deflated through the inflation lumen 36.

The deployment balloon catheter 30 terminates at its distal end in luer locks 38A and 38B which are connected by means of a standard bifurcated connector 39 to the proximal end of the catheter shaft 32. The luer lock 38A is in fluid communication with the inflation lumen 36 and the luer lock 38B communicates with the guide wire lumen 34. Balloon catheters of this construction are conventional; therefore, the deployment catheter 30 is not described in further detail.

The lead balloon catheter 40 likewise is of conventional construction and includes an elongated flexible shaft 42 which includes a guide wire lumen 44 and an inflation lumen 46. A lead balloon 48 is mounted at the distal end of the catheter 40 and can be selectively inflated and deflated through the inflation lumen 46. A luer lock 49 is attached to the proximal end of the lead balloon catheter 40 so that the balloon 48 can be inflated by the introduction of fluid through the luer lock 49.

The lead balloon shaft 42 includes an opening 50 which, as most clearly shown in FIG. 4, is adapted to receive the distal end of the deployment catheter 30. Opening 50, which may be formed by skiving shaft 42, does not affect the inflation lumen 46 but enables the guide wire lumens 34 and 44 to be aligned in a substantially colinear relationship so that a standard guide wire 52 can be passed from the lead balloon catheter 40 to the guide wire lumen 34 of the deployment catheter 30 during use.

As shown schematically in the drawings, sheath 20 has a constant outer diameter, but the inner diameter of the proximal portion of the sheath (FIG. 1A) is less than the inner diameter of the distal portion (Fig. 1B), i.e. the distal section is more flexible (less stiff) and includes a wider lumen. The proximal portion of the sheath provides increased pushability and torquability of the catheter as it is inserted. Because the graft stent complex is muzzle loaded (as explained below), there is no need for a large internal diameter in the proximal segment of sheath 20 and a thicker wall is feasible.

In the distal portion of the sheath 20, the wall is thin and indeed, may even be flimsy, for example, comparable to cellophane film. Reduction of wall thickness in the distal portion of the sheath provides increased space in which the graft stent complex can be housed, which means that for a given outer diameter, a larger complex is possible with the invention. Pushability of the catheter is enhanced in part by the presence of the stent graft complex within the sheath but, primarily, the stiffness required is achieved by pressurizing the sheath by the introduction of fluid under pressure through port 26 of valve 21. By monitoring the pressure on a manometer 54 during insertion of the sheath, the surgeon can continuously vary the stiffness (and thus pushability and flexibility) of the sheath throughout the insertion procedure. This means that the surgeon has the capability of varying the stiffness of the catheter sheath during different phases of insertion depending on the degree of tortuously of the vascular system.

The sheath 20 may be made of PTFE (Teflon). The length and characteristics of the sheath will vary depending upon the particular application. Where an aortic aneurysm graft is to be deployed, the sheath 20 may be approximately 60 cm in length with the distalmost 15–20 cm comprising the flexible portion of the sheath. The sheath may be manufactured by standard extrusion techniques with the distal flexible portion thereafter cored from the extruded tube to form a thinner-walled flexible section.

The device may be assembled and sold in the condition shown in FIGS. 1A and 1B, or it may be assembled at the time of use. The method of assembly is as follows.

Deployment catheter 30 and lead balloon catheter 40 are passed through the deployment catheter port 22 and tip catheter port 24 of hemostatic valve 21 with the valve screws 22A and 22B open until the balloons 38 and 48 extend from the distal end of the sheath. If the device is to be used to deploy a graft stent complex 12, 14, the complex is then placed over the distal end of deployment catheter 30 with the balloon 38 beneath the stent 14. In conventional fashion, the stent 14 is crimped to balloon 38. The distal tip of deployment catheter 30 is then inserted into the opening 50 within the shaft 42 of lead balloon catheter 40 so that a continuous or colinear passageway is formed between the guide wire lumens 34 and 44.

The graft stent complex and catheters 30 and 40 are then muzzle loaded into the sheath 20 (i.e., retracted proximally into the sheath) and positioned so that, for example, about half of the lead balloon 48 extends from the distal end of the sheath 20, as shown in FIG. 2B. The lead balloon 48 may be about four cm. in length which means that approximately two cm. of the balloon will extend distally from the sheath 20. The ability to muzzle load the catheters and graft-stent complex into the sheath is a valuable feature of the invention since it avoids the need to push the graft through the entire sheath which, in view of the length of the sheath, can be time consuming and may result in separation of the graft-stent complex (14,12) from the underlying balloon.

The device is used as follows. A one-way valve 51 (FIG. 2A) is attached to the lead balloon inflation port luer lock 49 and the lead balloon 48 inflated with saline solution from a standard ten cc. syringe 53 attached to luer lock 49. As shown in Fig. 2B, when the balloon 48 is inflated, it seals the distal end of the sheath 20 and provides a smooth taper which facilitates movement of the sheath through the patient's vasculature. Expansion of the balloon also results in a smooth transition between the sheath and balloon (see FIG. 2B) which means that the sheath is less likely to injure the artery or dislodge thrombus or plaque as it is pushed through the artery. The lead balloon also serves to aid in hemostasis, since blood cannot travel back through the sheath and out of the patient while the balloon is inflated.

The syringe 28 attached to the sheath pressurization port 26 is then used to inject saline into sheath 20 to a desired sheath pressure as measured by the infusion pressure manometer. After all air has been evacuated, i.e. the system has been bled, the catheter infusion ports are closed. The device is now ready to be inserted into the patient.

The device is inserted as follows. First, the guide wire 52 is passed through the patient's vasculature with its location being confirmed fluoroscopically. In FIGS. 5A, 5B, 6A and 6B, a blood vessel is shown at 56 for purposes of explanation. The operator then inserts the proximal end of the guide wire into the distal end of the guide wire lumen 44 within lead balloon catheter 40. The operator next introduces sheath 20 into the patient over the guide wire. Because of the way in which the deployment catheter 30 is nested within the lead balloon catheter 40, the guide wire passes from the lead balloon guide wire lumen 44 into the colinear deployment guide wire lumen 34 as shown in FIG. 4. With the inflated lead balloon 48 providing a smooth taper for the pressurized sheath 22, the operator guides the sheath with the enclosed catheters to the location where the stent is to be deployed. As the sheath is being moved, the surgeon can vary its flexibility to accommodate the specific vasculature by adjusting the pressure within the sheath as indicated by manometer 54. The sheath position is determined fluoroscopically in a conventional fashion. For example, the sheath 20 may have regularly placed radiopaque markers so that the exact location of the sheath tip can be identified. When the proper location is reached, lead balloon 48 is deflated using the syringe.

The thumbwheel 24A for the lead balloon catheter 40 is then released and the lead balloon catheter advanced distally (with the position of the deployment catheter 30 held in place) until the catheter 40 is disengaged from the guide wire 52 (FIGS. 5A and 5B). This occurs when the opening 50 moves distally beyond the distal end of the guide wire 52.

The surgeon then retracts the lead balloon catheter 40 back into the sheath 20 to a position proximal of the graft stent complex 12, 14 and tightens the thumb screw 24A to retain the lead balloon catheter in this position.

Next, the thumb screw 22A which secures the deployment catheter 30 is loosened and the sheath 20 retracted to expose the stent 14. The syringe with saline is attached to the luer lock 38B and the deployment balloon 38 is expanded to deploy the stent (FIGS. 6A and 6B). After the stem is fully deployed, the deployment balloon 38 is deflated. It may then be exchanged for a second deployment catheter containing a second stent to be properly positioned with respect to the graft 12 and deployed. Alternatively, graft 12 may be provided with both stents, in which case the deployment catheter 30 can be withdrawn until the deployment balloon 38 is beneath the second stent. The balloon can then be expanded to deploy the second stent. The sheath 20 and catheters 30 and 40 are then removed and a completion angiogram performed.

In the embodiment of FIGS. 7–9 only a single catheter is used. In this embodiment, the catheter comprises an elongated flexible shaft 60 having a central guide wire lumen 62 and peripheral inflation lumens 64 and 66. A lead balloon 68 is provided at the distal end of the catheter 60 for inflation through the lumen 64. A deployment balloon 70 is positioned on the shaft 60 proximally of the lead balloon 68 and adapted to be inflated or deflated by means of the lumen 66. The lead balloon 68 and deployment balloon 70 function the same way as the lead balloon 48 and deployment balloon 38 of the embodiment shown in FIGS. 1–6 but, of course, cannot be separated.

The proximal end of the guide sheath 20 terminates in a hemostatic valve 72 through which the catheter shaft 60 extends. The hemostatic valve 72 includes a port 74 which may be connected to the syringe 28 shown in FIG. 1A. The port 74, of course, provides access to the interior of the sheath 20. A standard hemostatic valve may be used as valve 72.

The catheter shaft 60 terminates in a conventional trifurcated firing 76 having three proximal ports which terminate in luer lock 78, 80, and 82. The luer locks 78 and 82 provide access to the inflation lumens 64 and 66, respectively, while the luer lock 80 provides access to the guide wire lumen 62. In this case the guide wire 52 is inserted in conventional fashion through the guide wire lumen 62 of the catheter shaft 60. A one-way valve would be connected to luer lock 78 to maintain the inflation of the lead balloon during use.

The components illustrated may be conventional. For example, hemostatic valve 21 may be an ANGEDAPT Y-connector manufactured by Angeion Medical Products, Model No. AYC-020. Hemostatic valve 72 may be of the type sold by Universal Medical Instrument Corp. under the trademark CATH-SEAL (Model No. 1200- 90-3003 ). The pressure syringe 28 may be a LeVeen disposable inflation syringe with pressure gauge manufactured by the MedTech Division of Boston Scientific (Model No. 15-101).

In the illustrated embodiments, the guide sheath comprises a relatively stiff flexible portion and a relatively flexible distal portion. It is conceivable that it may prove beneficial to have a continuously variable change in stiffness/flexibility, in which case the inner wall may taper gradually with the diameter increasing from the proximal end to the distal end. It is also possible that stiffness/flexibility may vary in a number of discrete steps, rather than in a single step as illustrated.

It is also contemplated that the entire sheath can be made of a highly flexible plastic (e.g., PTFE), which can be folded so as to reduce its cross section prior to insertion. The advantage of this construction is that a small introducer (and thus a smaller hole in the patient's artery) could be used to introduce the sheath into the patient's artery. Once in position, the sheath would be pressurized as described in the foregoing to increase its diameter as required for delivery and deployment of the stent.

In addition to varying the pressure of the sheath as it passes through the patient's vasculature, it is also possible to vary the pressure applied to the lead balloon so that the operator can vary the flexibility of the leading surface of the sheath as it traverses the vasculature, should this be desirable.

In the process of retracting the sheath so that the stent can be deployed, the possibility exists that the stent may be moved accidentally with respect to the patient's artery. FIGS. 10–12 illustrate a handle mechanism which, in use, reduces the likelihood of stent displacement when the physician retracts the sheath.

FIGS. 10–12 illustrate a handle construction for use with the two balloon embodiment shown in FIGS. 7–9 although the handle would have equal utility with the two catheter embodiment of FIGS. 1–6. In FIGS. 10–12 the same numerals are used to identify corresponding parts although some parts are illustrated as slightly different in appearance.

As shown in FIGS. 10–12, the proximal end of the sheath 20 is slidably retained within a handle 100 which includes an elongated slot 102 through which port 74 of the hemostatic valve 72 extends. The catheter shaft 60 extends through a locking screw 104 attached to the proximal end of the handle 100 and through a locking screw 106 of the hemostatic valve 72 into the sheath 20. The hemostatic valve includes a distal stop 108 adapted to abut against the distal edge 109 of slot 102 and a proximal stop 110 adapted to abut against the proximal edge 111 of slot 102.

In use, hemostatic valve 72 is pushed distally until the stop 108 abuts edge 109 of slot 102. The locking screw 106 is loosened to permit movement of the valve 72 relative to the catheter shaft 60. Locking screw 104, however, is tightened so that the handle 100 cannot move relative to the catheter shaft 60.

After the stent has been positioned as explained above, and it is time to retract the sheath so that the stent can be deployed, the physician holds the handle in one hand and pulls back on the port 74 until stop 110 abuts against the edge 111 of slot 102. Because the locking screw 104 retains the catheter 60 with respect to the handle 100, the sheath 20 is moved relative the catheter 60 the distance determined by the length of slot 102 and the positions of the stops 108 and 110. This permits the physician to hold the catheter 60 (and thus the stent) in a fixed location and withdraw the sheath by a precise amount. Therefore, the likelihood of human error causing improper positioning of the stent when the sheath is retracted is reduced.

When the sheath is pressurized, a substantial pressure is applied to the lead balloon which, obviously, must not be expelled when the sheath is pressurized. Accordingly, as shown in FIG. 13, to aid in retaining the lead balloon 48 within sheath 20, the inner surface of the distal end of sheath 20 and the outer surface of the lead balloon 48 may be provided with mating circumferential ribs and grooves. These grooves may extend over about ½ inch and will prevent accidental expulsion of the lead balloon when sheath 20 is pressurized. Other comparable means may be used to retain the expanded lead balloon within the pressurized sheath 20.

FIGS. 14 shows an embodiment of the invention in which the lead balloon is mounted on a separate lead balloon catheter adapted to be introduced into the distal end of the sheath. The construction of FIG. 14 is designed for use in a novel stent deployment procedure, described below, which is of special utility with patients having a tortuous vasculature through which it is difficult to move a stent deployment catheter. Before describing the procedure, the catheter construction is described. In FIG. 14, parts corresponding to the parts shown in the embodiment of FIGS. 7–9 bear the same numbers. In this embodiment, the catheter 60 serves as a stent deployment catheter. It supports an inflatable balloon 70 on which stent 14 is mounted for deployment as explained above. Balloon 70 and stent 14 are retained within the sheath 20 which may be pressurized as described above.

The lead balloon 68 is on a separate lead balloon catheter 120. The adjoining ends of the lead balloon catheter 120 and the deployment catheter 60 can be connected together in any suitable fashion which enables the catheters to be selectively connected and disconnected. For example, the end of lead balloon catheter 120 may be tapered and include a circumferential 122 detent adapted to engage a mating rim 124 on the deployment catheter 60 so that the two catheters are held securely together, as shown in detail in FIG. 14A. Numerous other connecting means such as bayonet type connecters, threaded connectors, etc. can be used. The object is to make sure that the two catheters are securely held together during use but, as explained below, in such a way that they can be separated when it is necessary to withdraw them from the patient's vasculature.

In cross section, the catheter 60 and 120 may be similar to the cross section shown in FIG. 8 with a central lumen through which a guidewire 52 passes. In each case, only a single inflation lumen 64 (or 66) is necessary.

A small port 126 may be provided in the catheter 120 for the purpose of introducing an angiographic contrast material as described in further detail below. When a contrast material is to be introduced through the catheter, a conventional one-way valve (not shown) should be provided in front of the port 126 (to the right of the port as illustrated in FIG. 14) so that the contrast material introduced into the central lumen will be blocked from flowing through the guide wire lumen and thus will exit through the port 126.

The catheter construction of FIG. 14 is designed to enable two physicians to simultaneously push and pull the deployed stent through the patient's vasculature. This is particularly beneficial in the case of patients with tortuous arteries as frequently encountered in the case of elderly patients. The way in which this is achieved is explained in the following.

Using a needle puncture technique a needle is inserted into the brachial artery in the patient's arm through a percutaneous approach. This needle is guided by palpating the pulse of the brachial artery and thereby advanced into the lumen of the artery. Through this needle, guidewire 52 is inserted and advanced into the lumen of the artery. Under fluoroscopic control, the guidewire is advanced retrograde (against the flow of blood) within the brachial artery to the axillary artery. From the axillary artery the wire moves directly into the left subclavian artery which connects directly with the thoracic portion of the aorta. When the wire has entered the aorta in this retrograde fashion, it is advanced under fluoroscopic control down the thoracic aorta into the abdominal aorta. Once it has reached the distal end of the abdominal aorta it is selectively directed into either the right or left common iliac artery. The side into which the wire is directed depends upon which artery has been chosen for subsequently advancing the sheath 20 and the stent deployment catheter 60. Generally, the larger of the two iliac arteries is chosen as the access vessel.

The wire 52 is then advanced under fluoroscopic control down through the common iliac artery into the external iliac artery and finally into the common femoral artery. Once the wire has reached the common femoral artery an incision is made into the common femoral artery. The wire is visualized and drawn out of this incision and left coiled outside the body. At this point one end of a very long wire is coiled outside of the femoral artery in the groin and the other end of this very long wire is coiled outside the body through a percutaneous puncture of the brachial artery in the left arm.

Using an over-the-wire technique, the lead balloon catheter 120 is advanced through the percutaneous puncture in the left brachial artery over the wire through all the vessels previously described down through the aorta and out the appropriate iliac artery, continuously following the guidewire 52. Once the balloon has emerged out of the common femoral artery, the stent deployment device is ready for use. The tip of lead balloon catheter 120 is inserted into the distal end of deployment catheter so that the detent 122 and ridge 124 are locked together to form a fight union. After this union has been established, the lead balloon catheter 120 is advanced into the distal end of the sheath 20 so that approximately half of the balloon 168 is inside the sheath while the remaining half of the balloon is outside the sheath. The lead balloon 68 is then inflated to maximum pressure thereby providing a smooth taper at the distal end of sheath 20.

With the lead balloon 68 fully inflated and locked into position, the distal end of the sheath 20 and lead balloon are carefully inserted into the previously created arteriotomy in the femoral artery. This process is done by slowly pulling back slack on the lead balloon catheter 120 in the arm as the sheath 20 is advanced into the femoral artery and then retrograde into the external iliac artery.

The sheath 20, at this juncture, is then pressurized to an appropriate pressure as previously described to produce an optimized balance of flexibility and pushability. Once pressurization of the sheath 20 has been accomplished, by gently pulling on the lead balloon catheter 120 at its origin in the brachial artery while simultaneously pushing the sheath 20 from its distal end into the iliac artery, the entire system is advanced from the iliac arteries into the abdominal aorta and into a suitable position for deployment of the stent graft.

When the sheath 20 has reached the appropriate position in the abdominal aorta, the lead balloon 60 is deflated. The sheath 20 covering the stent 14 is then withdrawn to expose the stent and graft. To ensure exact positioning of the stent in an appropriate position in relationship to surrounding branch arteries, an arteriogram may be performed. This arteriogram is performed as follows.

The guide wire 52 which extends from the brachial artery to the common femoral artery is first removed. The one way valve in the tip of the lead balloon catheter 120 permits only retrograde fluid flow in the catheter. Removing the guide wire 52 closes the valve mechanism permitting pressurization of the central lumen of the lead balloon catheter 120. Angiographic contrast material is injected through the external port of lead balloon catheter 120 into the guide wire lumen of the catheter and exits from port 126 in the catheter shaft. Contrast cannot continue down the balloon catheter shaft because the closed valve occludes the passage way. This angiogram injection will permit final localization of the appropriate position for the stent graft.

Once the angiogram has been completed, the guide wire 52 is then reinserted through the groin and out through the brachial artery. At this point, sheath 20 is retracted and the deployment balloon 70 inflated to deploy the stent 14. During inflation of the deployment balloon 70, tension is maintained on the lead balloon catheter shaft 120 (with lead balloon 68 deflated). By so doing, distal migration of the stent and deployment balloon secondary to the downward motion of the pumping circulation, can be avoided. Traction on the lead balloon catheter 120 which is attached the deployment balloon 60 will aid in the stabilization of this balloon during deployment and prevent distal migration. Once the proximal stent of the stent graft has been deployed, the catheters 120 and 60 are disconnected either by applying gentle opposite tension to both balloon catheter shafts or by advancing the tips of both catheters out of the common femoral artery where they can be disengaged manually. Additional procedures including the placement of additional stents could then be performed using well described standard techniques.

The foregoing description relates to the deployment of an aortic stent graft or stent but the principals of the invention may be used for the passage of other transluminal devices into other vascular systems using this push-pull technique.

Many modifications of the illustrated embodiments are possible within the scope of the invention. For example, the stent deployment means may comprise a mechanical device rather than a balloon. One suitable device for mechanically deploying a stent is shown in copending U.S. patent application Ser. No. 08/196,278, filed Feb. 10, 1994, in the names of Michael and Ralph Marin, and entitled APPARATUS AND METHOD FOR DEPLOYMENT OF RADIALLY EXPANDABLE STENTS BY A MECHANICAL LINKAGE. Now U.S.Pat. No. 5,443,477.

Furthermore, although the invention has been described for use in the delivery and deployment of stents and graft stent complexes, the broad principles of the invention can be used in the delivery and/or deployment of other intraluminal devices such as but not limited to VenaCava filters, atherectomy devices and the like.

Instead of using a guide wire, a balloon catheter may be introduced into the thoracic aorta and the balloon expanded to permit the blood flow to push the catheter distally to a desired location such as the common femoral artery. The right or left artery can be selected by applying pressure to one artery causing the balloon to move to the other. The catheter can then be pulled from the artery and used as explained above or in any desired way to simultaneously push and pull an intraluminal device through the patient's arteries.

What is claimed is:

1. A method for introducing a transluminal device into a blood vessel, comprising the steps of:

causing a guide wire to enter the blood vessel at an entrance point;

passing the guide wire through the blood vessel;

causing the guide wire to exit the blood vessel at an exit point;

passing a first catheter over said guide wire with the ends of said catheter protruding from said entrance and exit points;

connecting a second catheter containing said transluminal device to said first catheter; and positioning said transluminal device within said blood vessel by pushing said second catheter and pulling said first catheter.

2. A method for introducing a transluminal device into a blood vessel, according to claim 1, comprising;

deploying said transluminal device into said blood vessel after it has been properly positioned;

disconnecting said first and second catheters; and removing one of said catheters through said entrance point and the other of said catheters through said exit point.

3. A method for introducing a transluminal device according to claim 1, wherein said second catheter is positioned within a guide sheath and said first catheter includes a lead balloon, said method further including the step of inserting the lead balloon into said guide sheath after said catheters have been connected and inflating said lead balloon to provide a tapered leading surface for said guide sheath.

4. A method for introducing a transluminal device according to claim 1, wherein said second catheter is positioned within a guide sheath and said first catheter includes a lead balloon, including the step of inserting the lead balloon into said guide sheath after said catheters have been connected and inflating said lead balloon to provide a tapered leading surface for said guide sheath.

* * * * *